US012746080B2

(12) United States Patent
Frishman et al.

(10) Patent No.: US 12,746,080 B2
(45) Date of Patent: Sep. 29, 2026

(54) EXTENDING REACH INSIDE THE MRI-BORE: A 7-DOF LOW-FRICTION, HYDROSTATIC TELEOPERATOR

(71) Applicant: The Board of Trustees of the Leland Stanford Junior University, Stanford, CA (US)

(72) Inventors: Samuel Frishman, Stanford, CA (US); Mark R. Cutkosky, Palo Alto, CA (US); Bruce L. Daniel, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 148 days.

(21) Appl. No.: 18/779,338

(22) Filed: Jul. 22, 2024

(65) Prior Publication Data

US 2024/0374326 A1 Nov. 14, 2024

Related U.S. Application Data

(63) Continuation of application No. 17/770,012, filed on Apr. 18, 2022, now Pat. No. 12,044,757, and a continuation of application No. 17/671,984, filed as application No. PCT/US2020/060138 on Nov. 12, 2020, now abandoned.

(60) Provisional application No. 63/149,455, filed on Feb. 15, 2021, provisional application No. 62/935,972, filed on Nov. 15, 2019.

(51) Int. Cl.
*A61B 34/35* (2016.01)
*A61B 10/02* (2006.01)

(52) U.S. Cl.
CPC .......... *A61B 34/35* (2016.02); *A61B 10/0233* (2013.01)

(58) Field of Classification Search
CPC ..... A61B 34/35; A61B 10/0233; A61B 34/30; A61B 34/37
See application file for complete search history.

(56) References Cited

U.S. PATENT DOCUMENTS

| | | | |
|---|---|---|---|
| 7,155,316 | B2 | 12/2006 | Sutherland |
| 10,895,271 | B2 | 1/2021 | Ings |
| 11,027,434 | B2 | 6/2021 | Larose |
| 2004/0111183 | A1 | 6/2004 | Sutherland |
| 2008/0276746 | A1 | 11/2008 | Seibold |
| 2017/0367776 | A1 | 12/2017 | Kwok |

(Continued)

OTHER PUBLICATIONS

Robots get a light touch, Feb. 2018.

*Primary Examiner* — Rochelle D Turchen
(74) *Attorney, Agent, or Firm* — LUMEN PATENT FIRM

(57) ABSTRACT

A teleoperated MRI compatible arm system is provided that allow a physician to remotely operate. The system is passive, meaning forces and motions are generated by the operator and the device transmits them through a low-friction hydraulic transmission to the output end. The device enables manipulation in seven axes and exhibits one-to-one motion, allowing the physician to position and orient the needle during insertion. Moreover, the system is back-drivable and passively reflects patient respiratory motions and forces, a major roadblock to other devices explored in this space. The configuration of degrees of freedom and inputs allows the manipulation arm to maintain contact with the skin while also allowing the operator to insert the needle.

11 Claims, 5 Drawing Sheets

(56) References Cited

U.S. PATENT DOCUMENTS

| | | | | |
|---|---|---|---|---|
| 2020/0046450 | A1 | 2/2020 | Tsao | |
| 2021/0007817 | A1 * | 1/2021 | Dong | F15B 15/1452 |

* cited by examiner

EXTENDING REACH INSIDE THE MRI-BORE: A 7-DOF LOW-FRICTION, HYDROSTATIC TELEOPERATOR

CROSS-REFERENCE TO RELATED APPLICATIONS

This application is a continuation of U.S. patent application Ser. No. 17/671,984 filed Feb. 15, 2022, which is incorporated herein by reference. U.S. patent application Ser. No. 17/671,984 priority from U.S. Provisional Patent Application 63/149,455 filed Feb. 15, 2021, which is incorporated herein by reference.

This application is a continuation of U.S. patent application Ser. No. 17/770,012 filed Apr. 18, 2022, now U.S. Pat. No. 12,044,757, which is incorporated herein by reference. U.S. patent application Ser. No. 17/770,012 is a 371 of PCT application PCT/US2020/060138 filed Nov. 12, 2020. PCT application PCT/US2020/060138 claims the benefit of U.S. Provisional application 62/935,972 filed Nov. 15, 2019.

STATEMENT OF GOVERNMENT SPONSORED SUPPORT

This invention was made with Government support under contract 1615891 awarded by the National Science Foundation. The Government has certain rights in the invention.

FIELD OF THE INVENTION

This invention relates to methods, devices and system for in-bore Magnetic Resonance Imaging (MRI) guided biopsies.

BACKGROUND OF THE INVENTION

Magnetic resonance (MR) offers safe, high contrast imaging of soft tissue inside the body, often superior to ultrasound (US) and computed tomography (CT). Today, MRI is predominantly used for diagnostic and preoperative imaging with limited ability to leverage it for guidance during surgical intervention. Poor access inside the MRI bore prohibits tool manipulation while patients remain inside the machine. In current biopsies conducted with MRI guidance, patients are removed from inside the bore for needle insertion and adjustment. The procedure is conducted step-wise, with incremental needle advancement between imaging scans and the patient repeatedly moved in and out of the bore. The present invention addresses the current shortcomings with an MRI compatible teleoperator that provides remote access inside the machine from several meters and enables needle manipulation without the need to remove the patient between imaging scans.

SUMMARY OF THE INVENTION

In one exemplary embodiment, this invention focuses on a teleoperated MRI compatible arm system that a physician can operate remotely from several meters. The system is passive, meaning forces and motions are generated by the operator and the device transmits them through a low-friction hydraulic transmission to the output end. The device enables manipulation in seven axes and exhibits one-to-one motion, allowing the physician to position and orient the needle during insertion. Moreover, the system is back-drivable and passively reflects patient respiratory motions and forces, a major roadblock to other devices explored in this space. The configuration of degrees of freedom and inputs allows the manipulation arm to maintain contact with the skin while also allowing the operator to insert the needle.

This technology pairs well one of the priority documents which is PCT/US2020/060138 filed Nov. 12, 2020.

By using the device as embodied herein, interventional radiologists at hospitals could perform in-bore MRI guided biopsies, improve procedure sensitivity and reduce current MRI biopsy procedure duration. Ultimately, this would improve the standard of care while reducing costs.

In another exemplary embodiment, the invention is characterized as a hydraulic teleoperator for remote access inside an imaging scanner bore (e.g. a Magnetic Resonance Imaging (MRI) scanner bore or a CT scanner bore). The hydraulic teleoperator has a base from which is attached a multiple degree of freedom mechanism. Each degree of freedom of the multiple degree of freedom mechanism is controlled by hydraulic joints having chambers connected to a first set of hydraulic fluid lines. The multiple degree of freedom mechanism is situated inside the imaging scanner bore. A teleoperator controls motions and forces of the multiple degree of freedom mechanism from a multiple degree of freedom control mechanism situated outside the imaging scanner bore. Further the hydraulic teleoperator has a single degree of freedom tool mechanism attached to a distal end of the multiple degree of freedom mechanism. The single degree of freedom tool mechanism is situated inside the imaging scanner bore where the single degree of freedom tool mechanism controls a tool. The motions and forces of the single degree of freedom tool mechanism are controlled via second set of hydraulic fluid lines to an operator input that is outside the imaging scanner bore.

In one example the multiple degree of freedom control mechanism outside the imaging scanner bore is a mirror, a scaled or a translated mechanism, or any combination thereof of the multiple degree of freedom serial chain mechanism inside the imaging scanner bore.

In a further example, the multiple degree of freedom mechanism is a serial chain with each degree of freedom being comprised of its own hydraulic joint connected to the first set of hydraulic lines.

In yet another example, the multiple degree of freedom mechanism has six degrees of freedom, resulting in a total of seven degrees of freedom adding the single degree of freedom of the tool mechanism and as such enabling arbitrary positioning of the tool mechanism in all six degrees of a 3D space.

In yet another example, the single degree of freedom tool mechanism is a biopsy needle insertion mechanism or an ablation needle insertion mechanism.

In yet another example, the single degree of freedom tool mechanism has at a distal end a skin contact point with a lumen for guidance of the tool.

In yet another example, the single degree of freedom tool mechanism has a pneumatic clutch for grip and release of a needle of the biopsy needle insertion mechanism or the ablation needle insertion mechanism.

In yet another example, the tool is a needle, and the single degree of freedom tool mechanism has a needle driver to translate the needle in insertion and retraction directions where the directions are defined in a longitudinal direction of the needle, and a needle holder to grip the needle via a retraction lock when a clutch mechanism of the needle driver releases the needle to hold a position of the needle during reposition of the needle driver.

In yet another example, the hydraulic fluid lines for each joint are crossed to achieve a one-to-one mapping of motion between the input and output.

In still another example, each chamber has a filling port and an exit port to mitigate trapped air in the hydraulic fluid lines and allowing fluid to be recycled during a filling process. The filling ports can house a one-way valve.

Embodiments of this invention have certain advantages:

1) As a multi-axis mechanism (i.e. arm), the workspace of the device enables biopsy of several organs.

2) The device can be passive (all energy can come from the operator and motions/forces can be mapped one-to-one between the input and output), reducing costs, regulations barriers, and safety concerns.

3) The device is back-drivable and exhibits force transparency (meaning the operator at the remote input can feel the forces occurring at the needle). This improves procedure accuracy and reduces procedure duration.

4) The device conforms to respiratory motions, making possible biopsy of organs in the torso.

DETAILED DESCRIPTION

Figure 1:
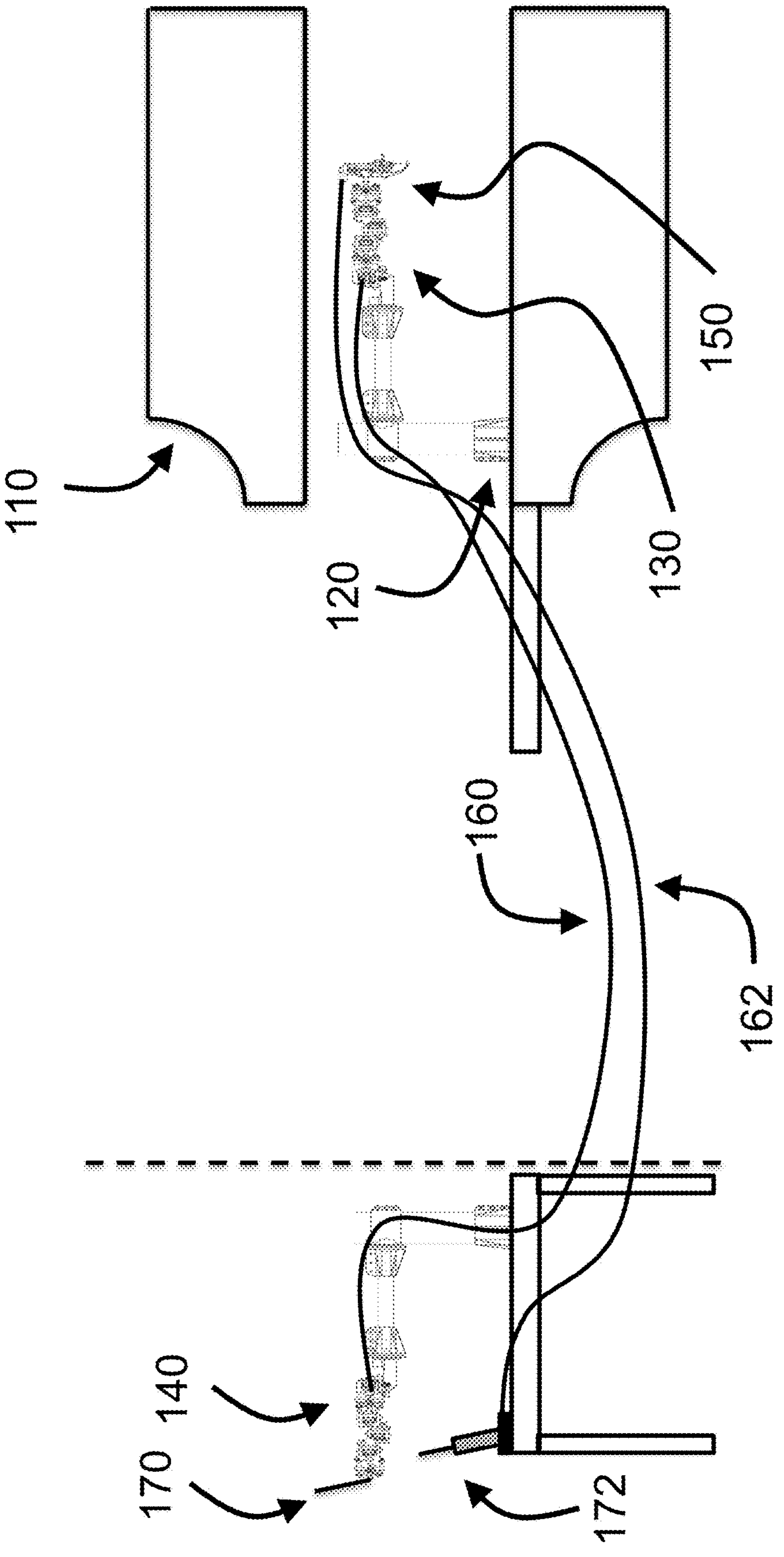
FIG. 1 shows according to an exemplary embodiment of the invention an overview of a first embodiment of the hydrostatic teleoperator for remote access inside a Magnetic Resonance Imaging (MRI) bore.
Figure 2:
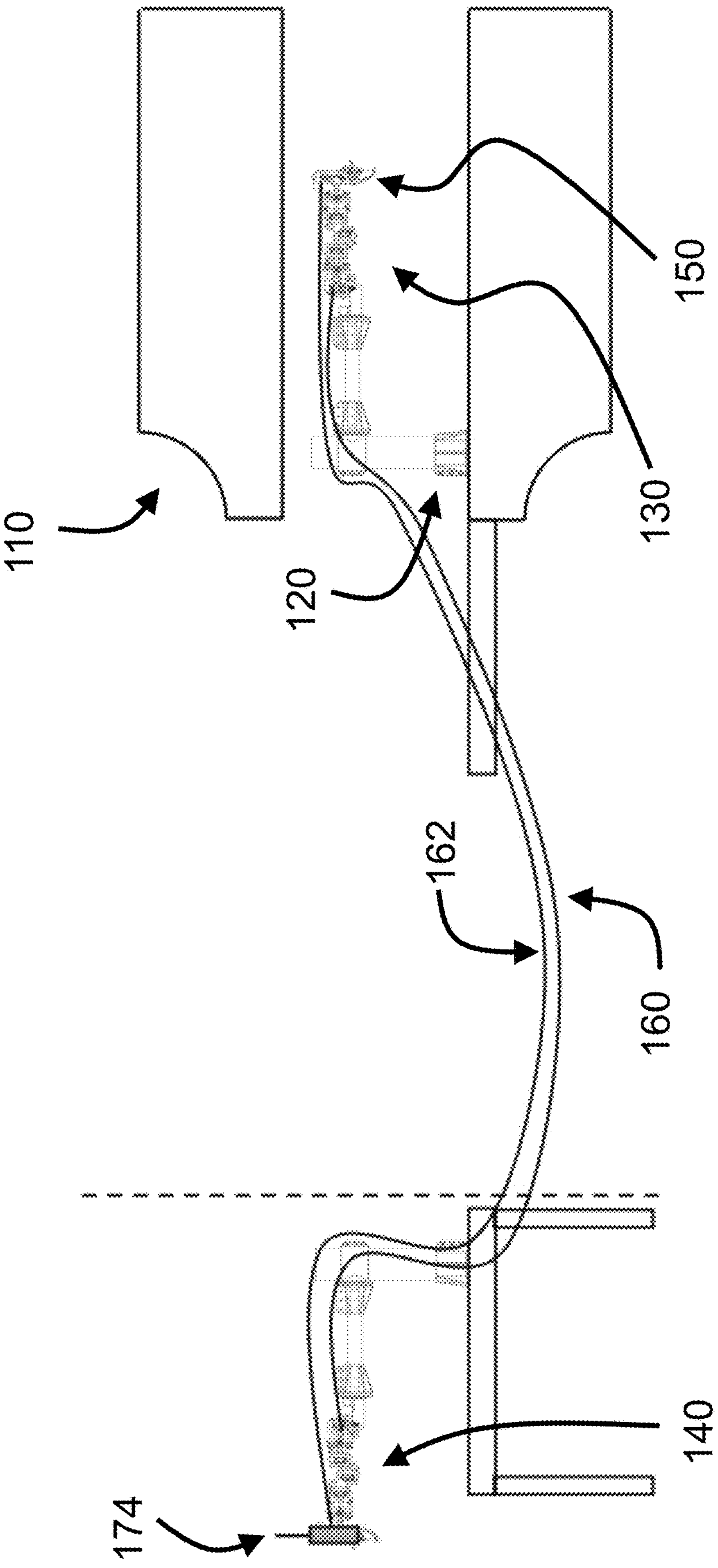
FIG. 2 shows according to an exemplary embodiment of the invention an overview of a second embodiment of the hydrostatic teleoperator for remote access inside a Magnetic Resonance Imaging (MRI) bore.

FIGS. 1-2 each show a schematic overview of the hydrostatic/hydraulic teleoperator for remote access inside a Magnetic Resonance Imaging (MRI) bore 110. A base 120 from which is attached a multiple degree of freedom serial chain mechanism 130, all situated inside the MRI bore. Each degree of freedom of the multiple degree of freedom serial chain mechanism is a joint having a chamber with of first set of hydrostatic fluid lines 160. A teleoperator via control 170 controls motions and forces of the multiple degree of freedom control mechanism 140 situated outside MRI bore 110. The multiple degree of freedom control mechanism 140 outside MRI bore 110 is a mirror or a translated mechanism of the multiple degree of freedom serial chain mechanism 130 inside the MRI bore. Mechanism 140 may additionally be scaled to amplify or reduce motion and or forces of mechanism 130.

A single degree of freedom tool mechanism 150 attached to a distal end of the multiple degree of freedom serial chain mechanism 130, wherein the single degree of freedom tool mechanism 150 is situated inside MRI bore 110 where the single degree of freedom tool mechanism 150 controls a tool (e.g., biopsy needle), wherein motions and forces of the single degree of freedom tool mechanism 150 are controlled via second set of hydrostatic fluid lines 162 to an operator input 172 (FIG. 1) or 174 (FIG. 2) that is outside MRI bore 110. Noted is that operator input 170 and 172 of FIG. 1 are combined as operator input 174 in FIG. 2.

Six-Axis Arm

Figure 3:
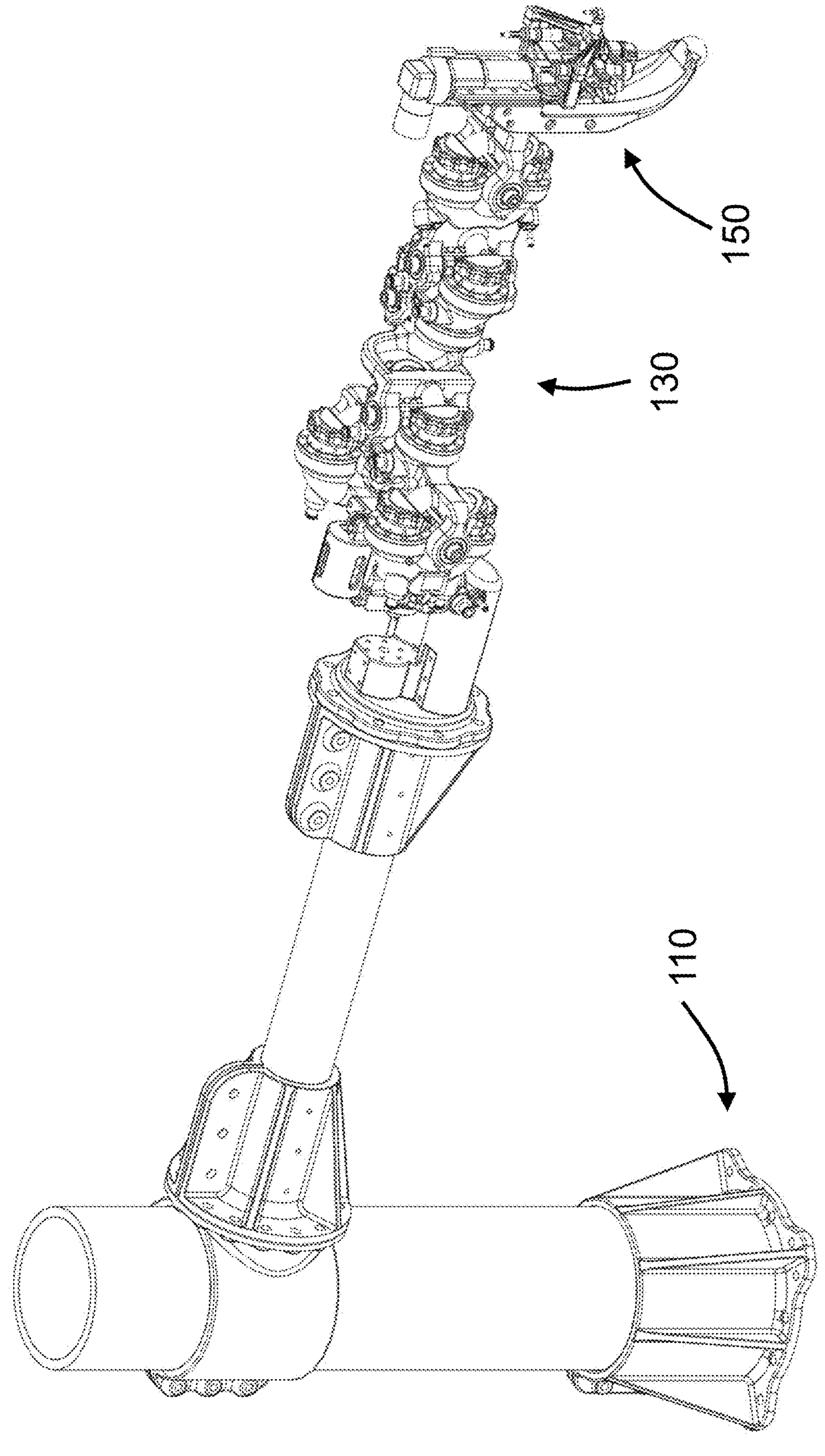
FIG. 3 shows according to an exemplary embodiment of the invention inside an MRI bore a base from which is attached a multiple degree of freedom serial chain mechanism as well as a single degree of freedom tool mechanism attached to a distal end of the multiple degree of freedom serial chain mechanism, which is also situated inside the MRI bore.

FIG. 3 illustrates a six-axis kinematic chain and link lengths 130 as shown earlier with respect to FIGS. 1-2. The dimensions are motivated by a workspace analysis and practical constraints arising from actuator size and tube fittings. The DOF order and configuration was designed to accommodate a low profile, an initial height less than the length of a 15 cm needle, and to favor a shorter distance between joints two and six. In particular, the roll joint (DOF one), was placed at the base. While this results in rotating the majority of the arm's mass, the lever experienced by joint two is reduced as compared to placing the roll joint at the end.

Filling lines with fluid and removing all air is a challenge in hydrostatic systems. To mitigate trapped air, each chamber includes a filling and exit port (FIG. 4D in Appendix C of priority document U.S. Provisional Patent Application 63/149,455), allowing fluid to be cycled through the system during the filling process. The filling ports house an MRI-safe one-way valve, providing a compact method for creating a self-closing inlet. Moreover, the one-way valves act as a mechanical safety, limiting the torque each joint can apply if pressure exceeds the maximum back pressure rating (300 psi), fluid bleeds through the one-way valve. Ball valves or other types of valves may be used if one-way valves are undesired or a higher-pressure rating is needed.

In this embodiment, each joint of the input and output arms are identical, with tubing connecting the respective joint chambers. Fluid lines of each joint are crossed, to achieve a one-to-one mapping of motion; a clockwise rotation at the input results in a clockwise rotation at the output. Actuation is transmitted with toroidal piston pairs, sealed by rotary rolling diaphragms. Linear rolling diaphragms may also be used with different mechanisms to convert motion. Apposing piston pairs enable operating the system at a nominal pressure which is necessary to maintain a convolution in the rolling-diaphragms. Moreover, the initial internal pressure dictates the maximum joint pull force as negative pressure is undesirable and can result in cavitation and diaphragm inversion. In opposing-piston systems, only one line must be hydraulic to provide necessary transmission stiffness and the other can be pneumatic. This reduce viscous losses and achieves a more responsive teleoperator, however, in the system provided herein, each line is water filled to avoid significant stored energy and potential patient or operator harm in the event of line rupture.

Figure 4:
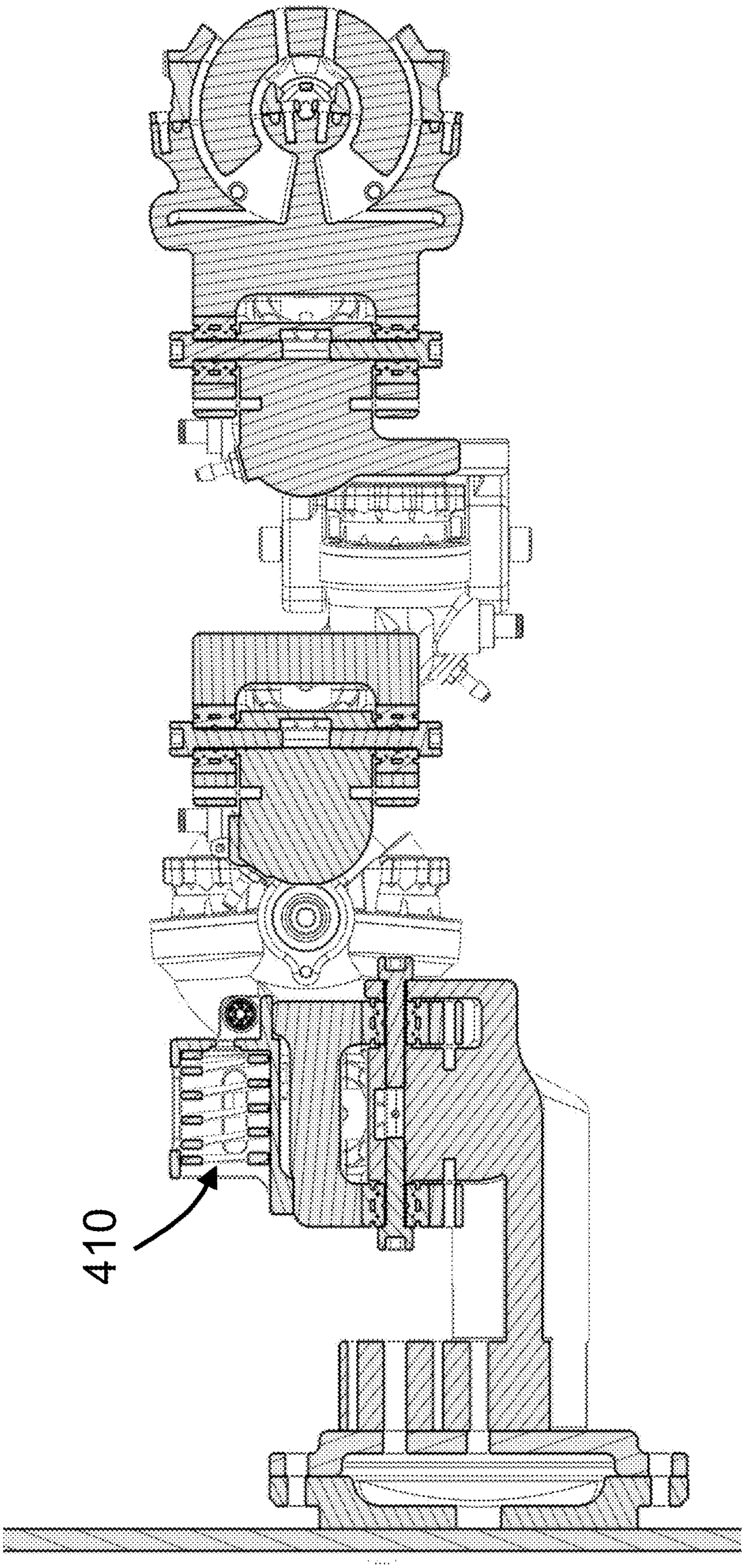
FIG. 4 shows according to an exemplary embodiment of the invention a cross-section view of the arm (multiple degree of freedom serial chain mechanism) illustrating the fluid chambers and toroidal pistons.

Counterbalancing: An ideal manipulator for transparent teleportation includes gravitational force compensation. In an exemplary design, Joint 2 is the degree of freedom most influenced by the arm's weight and in this prototype gravity compensation is only employed on this joint. This was achieved by using a plastic compression spring fixed to Joint 1. The compression spring 410 is illustrated in FIG. 4. A Dyneema line is attached to the end of the spring and anchored on joint 2. As joint 2 rotates, the spring is compressed, pulling the arm upward. This results in a design with the arm biased toward its neutral position (determined by the spring pre-load). An alternative approach provides a constant force creating a floating affect where the arm remains in balance at any configuration. Traditional constant force springs are incompatible with the MRI environment. Pneumatic cylinders could be used to achieve similar characteristics and are discussed in future work.

Insertion End Effector

A needle insertion mechanism mounts 150 to the end of the six-axis arm 130 and uses pneumatic clutch for grip and release of the needle. The insertion mechanism is controlled via a nearly frictionless transmission with precision ground glass cylinders as pistons. The glass cylinder transmission and pneumatic clutch was first introduced one of the priority documents which is PCT/US2020/060138 filed Nov. 12, 2020. A short summary is provided here. For average body mass index values, there is only 15-20 cm of space between the patient and bore wall, approximately the length of a standard biopsy needle. The clutch enables a compact design with actuation parallel to the needle and an initial configuration similar to the length of the needle. The needle is advanced through multiple short strokes, analogous to driving a needle directly in hand. The needle is gripped near the tip, inserted part way, re-gripped further up, and inserted deeper. Grip and release of the needle is achieved with a collet and is controlled by the operator via a foot-peddle valve. The operator manipulates the needle's insertion depth, and position of re-grip, via the glass cylinder transmission.

Figure 5:
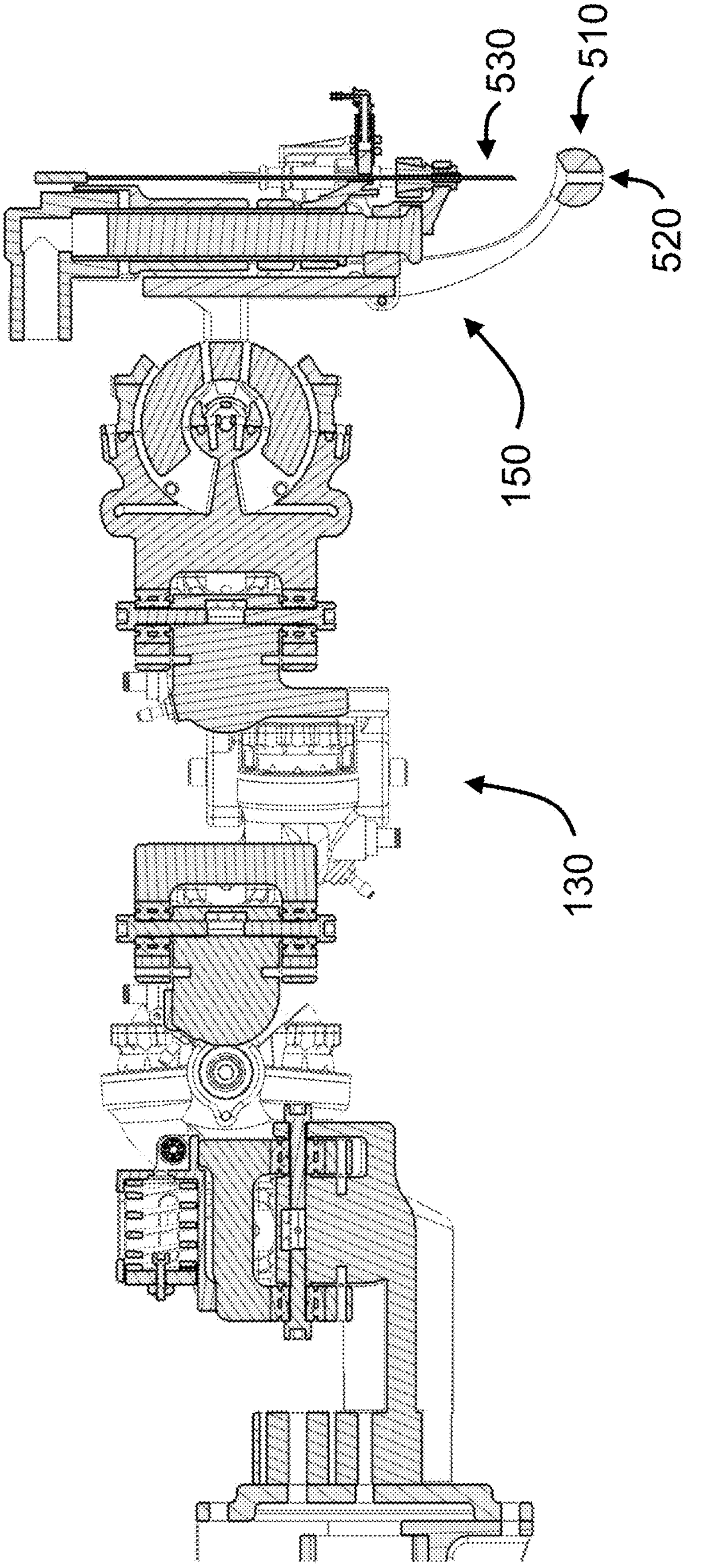
FIG. 5 shows according to an exemplary embodiment of the invention the single degree of freedom tool mechanism (aka insertion mechanism mounted to the multiple degree of freedom serial chain mechanism (aka arm). The mechanism includes a protruding beam which forms the contact with the skin surface and transmits body wall force to/from the arm. The tool or needle traverses through this point and is controlled with a custom, glass cylinder transmission and clutch.

The insertion mechanism includes a protruding beam that is initially positioned at the entry point on the skin. The single degree of freedom tool mechanism or insertion mechanism has at a distal end a skin contact point 510 with a lumen 520 for guidance of the tool or needle 530 (FIG. 5) The beam is fixed to the sixth joint of the arm and transmits forces from the body wall directly to the arm, rather than through the needle, and vice versa. This enables patient respiration to be reflected in the system and allows maintaining contact with the body wall while driving the needle; again similar to inserting a needle directly in hand. The distance the beam protrudes beyond the needle driver defines the maximum length of a single insertion stroke (FIG. 5). In this prototype, 3.5 cm was selected as a balance between overall length and insertion stroke. In other embodiments, the insertion mechanism may include clutching of other stroke lengths or no clutching system if the full insertion needed is achieved in one stroke. Additionally, the insertion mechanism may include other actuation schemes than the glass cylinders including rolling diaphragm or cable-based actuation.

What is claimed is:

1. A hydraulic teleoperator for remote access inside an imaging scanner bore, comprising:

(a) a base from which is attached a multiple degree of freedom mechanism, wherein each degree of freedom of the multiple degree of freedom mechanism is controlled by hydraulic joints having chambers connected to a first set of hydraulic fluid lines, wherein the multiple degree of freedom mechanism is situated inside the imaging scanner bore, and wherein a teleoperator controls motions and forces of the multiple degree of freedom mechanism from a multiple degree of freedom control mechanism situated outside the imaging scanner bore;

(b) a single degree of freedom tool mechanism attached to a distal end of the multiple degree of freedom mechanism, wherein the single degree of freedom tool mechanism is situated inside the imaging scanner bore where the single degree of freedom tool mechanism controls a tool, wherein motions and forces of the single degree of freedom tool mechanism are controlled via second set of hydraulic fluid lines to an operator input that is outside the imaging scanner bore, wherein the tool is a needle, and the single degree of freedom tool mechanism comprises a needle driver to translate the needle in insertion and retraction directions where the directions are defined in a longitudinal direction of the needle, and a needle holder to grip the needle via a retraction lock when a clutch mechanism of the needle driver releases the needle to hold a position of the needle during reposition of the needle driver.

2. The hydraulic teleoperator as set forth in claim 1, wherein the multiple degree of freedom control mechanism outside the imaging scanner bore is a mirror, a translated mechanism, or any combination thereof of the multiple degree of freedom mechanism inside the imaging scanner bore.

3. The hydraulic teleoperator set as set forth in claim 1, wherein the multiple degree of freedom mechanism is a serial chain with each degree of freedom being comprised of its own hydraulic joint connected to the first set of hydraulic lines.

4. The hydraulic teleoperator as set forth in claim 1, wherein the multiple degree of freedom mechanism has six degrees of freedom, resulting in a total of seven degrees of freedom adding the single degree of freedom of the tool mechanism and as such enabling arbitrary positioning of the tool mechanism in all six degrees of a 3D space.

5. The hydraulic teleoperator as set forth in claim 1, wherein the single degree of freedom tool mechanism is a biopsy needle insertion mechanism or an ablation needle insertion mechanism.

6. The hydraulic teleoperator as set forth in claim 1, wherein the single degree of freedom tool mechanism has at a distal end a skin contact point with a lumen for guidance of the tool.

7. The hydraulic teleoperator as set forth in claim 6, wherein the single degree of freedom tool mechanism has a pneumatic clutch for grip and release of a needle of the biopsy needle insertion mechanism or the ablation needle insertion mechanism.

8. The hydraulic teleoperator as set forth in claim 1, wherein the hydraulic fluid lines for each joint are crossed to achieve a one-to-one mapping of motion between the input and output.

9. The hydraulic teleoperator as set forth in claim 1, wherein each chamber has a filling port and an exit port to mitigate trapped air in the hydraulic fluid lines and allowing fluid to be recycled during a filling process.

10. The hydraulic teleoperator as set forth in claim 9, wherein the filling ports house a one-way valve.

11. The hydraulic teleoperator as set forth in claim 1, wherein the imaging scanner bore is a Magnetic Resonance Imaging (MRI) scanner bore or a CT scanner bore.

* * * * *